United States Patent [19]

Franz et al.

[11] 4,175,946
[45] Nov. 27, 1979

[54] THIO DERIVATIVES OF N-TRIFLUOROACETYL-N-PHOSPHONOMETHYLGLYCINE

[75] Inventors: John E. Franz, Crestwood; Robert J. Kaufman, University City, both of Mo.

[73] Assignee: Monsanto Company, St. Louis, Mo.

[21] Appl. No.: 922,900

[22] Filed: Jul. 10, 1978

[51] Int. Cl.$^2$ .............................................. A01N 9/36
[52] U.S. Cl. ....................................... 71/87; 260/941
[58] Field of Search ............................. 71/87; 260/941

[56] References Cited

U.S. PATENT DOCUMENTS

| | | | |
|---|---|---|---|
| 3,419,620 | 12/1968 | Becher et al. | 71/87 |
| 3,799,758 | 3/1974 | Franz | 71/86 |
| 3,853,530 | 12/1974 | Franz | 71/86 |
| 3,894,125 | 7/1975 | Beriger | 71/87 |
| 3,948,975 | 4/1976 | Franz | 71/86 |
| 3,970,695 | 7/1976 | Rueppel | 71/86 |
| 3,991,095 | 11/1976 | Gaertner | 71/87 |
| 4,042,370 | 8/1977 | Trueb | 71/86 |

*Primary Examiner*—Glennon H. Hollrah
*Attorney, Agent, or Firm*—William T. Black; Donald W. Peterson

[57] ABSTRACT

This disclosure relates to thio derivatives of N-trifluoroacetyl-N-phosphonomethylglycine esters, to herbicidal compositions containing same and to the herbicidal use thereof. The thio derivatives of N-trifluoroacetyl-N-phosphonomethylglycine esters are useful as herbicides.

24 Claims, No Drawings

THIO DERIVATIVES OF N-TRIFLUOROACETYL-N-PHOSPHONOME-THYLGLYCINE

This invention relates to N-trifluoroacetyl-N-phosphonomethylglycine thio derivatives, to herbicidal compositions containing same and to herbicidal methods. More particularly, this invention relates to N-trifluoromacetyl-N-phosphonomethylgycinate esters having thio groups bonded to the phosphorus atom thereof.

In accordance with U.S. Pat. No. 3,970,695, issued July 20, 1976, N-perfluoroacyl-N-phosphonomethylglycines of the formula

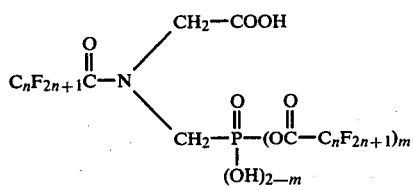

wherein n is an integer of from 1 to 4 and m is 1 or 0 are produced by reacting a perfluoroacyl anhydride with N-phosphonomethylglycine in the presence of a perfluoroalkanoic acid to form the compound of the formula wherein m is 1 and then by hydrolysis to form the compounds wherein m is 0.

N-phosphonomethylglycine, its salts, amides, esters and other derivatives are disclosed in U.S. Pat. No. 3,799,758 and are shown to be post-emergent herbicides. Other derivatives of N-phosphonomethylglycine and the plant growth regulation use thereof are disclosed in U.S. Pat. No. 3,853,530.

The novel N-trifluoroacetyl-N-phosphonomethylglycinate thio derivatives of this invention are those having the formula

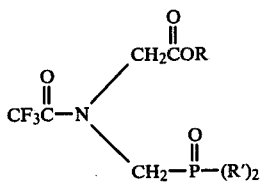

wherein R is an alkyl group containing from 1 to 10 carbon atoms, a chloro lower alkyl group containing from 1 to 4 carbon atoms and 1 to 3 chlorine groups, a lower alkoxy lower alkyl group containing from 3 to 6 carbon atoms or an alkoxyalkoxyalkyl group containing from 5 to 9 carbon atoms and R' is a member of the group consisting of lower alkylthio, lower alkenylthio, benzylthio, phenylthio, or substituted phenylthio wherein the phenyl group contains 1 to 2 substituents selected from the group consisting of halo, lower alkyl and lower alkoxy.

As employed herein, "chloro lower alkyl" designates those alkyl groups containing up through four carbon atoms in a straight or branched chains and up to three chlorine groups. The terms "lower alkyl" and "lower alkenyl" as employed herein define such groups containing up to and including four carbon atoms.

Illustrative of the alkoxyalkyl groups which R represents are methoxyethyl, methoxypropyl, methoxybutyl, ethoxyethyl, ethoxypropyl, propoxyethyl, propoxypropyl and the like. Illustrative of the alkoxyalkoxyalkyl groups represented by R are, for example, methoxyethoxyethyl, methoxyethoxypropyl, methoxypropoxypropyl, methoxypropoxybutyl, ethoxyethoxyethyl, propoxypropoxypropyl and the like.

The novel compounds of this invention are produced by reacting an ester dichloride of N-trifluoroacetyl-N-phosphonomethylglycine having the formula

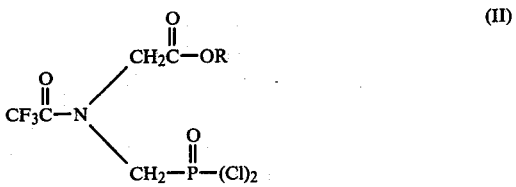

wherein R is as above-defined with a thio compound having the formula $$R'-S-H$$

wherein R' is as above-defined in an organic solvent and in the presence of a tertiary amine hydrogen chloride acceptor under essentially anhydrous conditions at a temperature of from about 10° C. to about 50° C. preferably at ambient temperatures.

In producing the compounds of this invention by the above reaction, the tertiary amine hydrogen chloride acceptor is preferably used in excess of stoichiometric to insure completeness of reaction. By the term "tertiary amine hydrogen chloride acceptor" as employed herein is meant tertiary alkylamines such as trimethylamine, triethylamine, tributylamine, trihexylamine and the like as well as aromatic tertiary amines such as pyridine, quinoline and the like.

The ratio of the reactants can vary over wide ranges. It is, of course, apparent to those skilled in the art that each chlorine atom in the N-trifluoroacetyl-N-phosphonomethylglycinyl dichloride will react with one thiol group (R'—S—H) and that, therefore, one would employ the reactants in equivalent amounts. When employing thiols which are volatile, it is sometimes desirable to employ an excess of the thiol. In other instances such with phenylthiols, it is sometimes preferred to use a slight excess of the glycinyl dichloride for ease of recovery of the product.

The substituted phenyl groups represented by R' are those containing 1 or 2 substituents selected from the group consisting of halogen, e.g., fluorine, chlorine and bromine; lower alkyl such as methyl, ethyl, propyl and butyl; and lower alkoxy such as methoxy, ethoxy, propoxy and butoxy groups and the like.

The ester dichlorides of Formula II employed as a reactant in producing the compounds of this invention are prepared by reacting an ester of N-phosphonomethylglycine of the formula

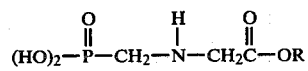

wherein R has the above-defined meaning with trifluoroacetic acid anhydride at temperatures of from about 10° C. to about 35° C., removing any excess anhydride and then treating the reaction product with excess thionyl chloride under refluxing conditions. The excess thionyl chloride is removed under vacuum to yield the dichlorides of Formula II.

The compounds of this invention are useful as herbicides.

The following non-limiting examples will serve to demonstrate to those skilled in the art the manner in which specific compounds within the scope of this invention can be prepared and their use as herbicides.

EXAMPLE 1

To a solution of α-toluenethiol (1.24 g, 0.01 mole) and triethylamine (1.01 g, 0.01 mole) in 30 ml. of dry ether was added dropwise and with good stirring ethyl N-trifluoroacetyl-N-(dichlorophosphonomethyl)glycinate (1.65 g, 0.005 mole) in 40 ml. of ether. After stirring at room temperature for 2 hours, the reaction mixture was filtered and the filtrate was concentrated in vacuo to give 2.45 g of a light yellow oil. This oil was extracted several times with hot petroleum ether to give upon concentration, ethyl N-trifluoroacetyl-N-(dibenzylthiophosphonomethyl)glycinate (2.05 g), $n_D^{25}=1.5609$.

Anal. Calc'd: C, 49.90; H, 4.59; N, 2.77; S, 12.69.
Found: C, 49.78; H, 4.71; N, 2.90; S, 12.95.

EXAMPLE 2

To a solution of ethyl N-trifluoroacetyl-N-(dichlorophosphonomethyl)glycinate (16.5 g, 0.05 mole) in 250 ml. of ether was added to a solution of thiophenol (11 g, 0.1 mole) and triethylamine (10.6 g, 0.105 mole) in 150 ml. of ether. After 1.5 hours, the reaction mixture was filtered and the filtrate was washed with water, dried over magnesium sulfate and concentrated in vacuo. The oil which resulted crystallized on standing to yield ethyl N-trifluoroacetyl-N-(diphenylthiophosphonomethyl)-glycinate (22.1 g) as a white solid, m.p. 50°–52° C.

Anal. Calc'd: C, 47.79; H, 4.02; N, 2.93; S, 13.43.
Found: C, 47.52; H, 4.24; N, 3.05; S, 13.38.

EXAMPLE 3

To a solution of ethyl N-trifluoroacetyl-N-(dichlorophosphonomethyl)glycinate (3.3 g, 0.010 mole) in 50 ml. of dry ether was added methanethiol (0.96 g, 0.02 mole) and triethylamine (2.02 g, 0.02 mole) in ether (50 ml.). The reaction mixture was stirred overnight at 20° C., then filtered. The filtrate was washed with 3% aqueous ammonium hydroxide, then dried over magnesium sulfate and concentrated in vacuo to afford ethyl N-trifluoroacetyl-N-(dithiomethylphosphonomethyl)glycinate as a white solid. The melting point when recrystallized from hexane was 50°–52° C.

Anal. Calc'd: C, 30.59; H, 4.28; N, 3.96; P, 8.77.
Found: C, 30.79; H, 4.50; N, 3.96; P, 8.72.

EXAMPLE 4

To a solution of ethyl N-trifluoroacetyl-N-(dichlorophosphonomethyl)glycinate (3.3 g, 0.01 mole) in 50 ml. of ether was added a solution of triethylamine (2.02 g, 0.02 mole) and butanethiol (1.8 g, 0.02 mole) in 50 ml. of ether. After two hours at 20° C., the solution was filtered and the filtrate washed with 3% aqueous ammonium hydroxide. The ether solution was concentrated in vacuo to afford an oil which was extracted into petroleum ether. Concentration of the petroleum ether extracts afforded the ethyl N-trifluoroacetyl-N-(dithiobutylphosphonomethyl)glycinate as a clear oil, $n_D=1.4830$.

Anal. Calc'd: C, 41.18; H, 6.22; N, 3.20; P, 7.08.
Found: C, 40.98; H, 6.29; N, 3.30; P, 6.83.

EXAMPLE 5

To a solution of ethyl N-trifluoroacetyl-N-(dichlorophosphonomethyl)glycinate (6.6 g, 0.02 mole) in 175 ml. of ether was added a solution of p-thioanisole (5.6 g, 0.04 mole) and triethylamine (4.04 g, 0.04 mole) in 75 ml. of ether. The reaction was stirred at 20° C. for 12 hours, filtered and the filtrate washed with 3% aqueous ammonium hydroxide. The filtrate was dried over magnesium sulfate and concentrated in vacuo. The residual oil was pumped at 0.005 mm. for 16 hours to remove a trace of p-thioanisole. Ethyl N-trifluoroacetyl-N-(di(p-methoxyphenylthio)phosphonomethyl)glycinate was recovered as an oil (8.8 g) $n_D^{22}=1.5773$.

Anal. Calc'd: C, 46.92; H, 4.31; N, 2.61; P, 5.76.
Found: C, 46.79; H, 4.48; N, 2.49; P, 5.60.

EXAMPLE 6

To a solution of ethyl N-trifluoroacetyl-N-(dichlorophosphonomethyl)glycinate (3.3 g, 0.01 mole) in 100 ml. of dry ether was added a solution of ethanethiol (1.24 g, 0.02 mole) and triethylamine (2.02 g, 0.02 mole) in 40 ml. of dry ether. The reaction was stirred for 16 hours at 20° C., then filtered. The filtrate was washed with 3% aqueous ammonium hydroxide, dried over magnesium sulfate and concentrated in vacuo to yield ethyl N-trifluoroacetyl-N-(dithioethylphosphonomethyl)glycinate (2.9 g) as a clear oil, $n_D^{22}=1.4857$.

Anal. Calc'd: C, 34.64; H, 5.02; N, 3.67; P, 8.12.
Found: C, 34.50; H, 4.90; N, 3.74; P, 8.08.

EXAMPLE 7

To a solution of ethyl N-trifluoroacetyl-N-(dichlorophosphonomethyl)glycinate (3.3 g, 0.01 mole) in 100 ml. of dry ether was added a solution of isopropylthiol (1.52 g, 0.02 mole) and triethylamine (2.02 g, 0.02 mole) in 60 ml. of ether. The solution filtered, washed with 3% aqueous ammonium hydroxide, dried over magnesium sulfate and concentrated in vacuo to yield ethyl N-trifluoroacetyl-N-(di(isopropylthio)phosphonomethyl)-glycinate (2.85 g) as a yellow oil, $n_D^{22}=1.4842$.

Anal. Calc'd: C, 38.14; H, 5.66; N, 3.42; P, 7.57.
Found: C, 38.06; H, 5.73; N, 3.47; P, 7.52.

EXAMPLE 8

Ethyl N-trifluoroacetyl-N-(di(n-propylthio)phosphonomethyl)glycinate was prepared by the procedure of Example 7, except n-propylthiol was used in place of isopropylthiol. Ethyl N-trifluoroacetyl-N-(di(n-propylthio)phosphonomethyl)glycinate was a yellow oil, $n_D^{22}=1.4862$.

Anal. Calc'd: C, 38.14; H, 5.66; N, 3.42; P, 7.57.
Found: C, 38.24; H, 5.83; N, 3.61; P, 7.51.

EXAMPLE 9

To a solution of ethyl N-trifluoroacetyl-N-(dichlorophosphonomethyl)glycinate (3.3 g, 0.01 mole) in 100 ml. of ether was added a solution of o-thiocresol (2.48 g, 0.02 mole) and triethylamine (2.02 g, 0.02 mole) in 50 ml. of ether at 20° C. The solution was stirred for 16 hours, then filtered. The filtrate was concentrated in vacuo and the residue was extracted into hot petroleum ether. Concentration of the petroluem ether extracts yielded ethyl N-trifluoroacetyl-N-(diorthotolylthiophosphonomethyl)glycinate as a white solid (4.58 g) which was recrystallized from methylcyclohexane, m.p. 79.5°–82° C.

Anal. Calc'd: C, 49.90; H, 4.59; N, 2.77; P, 6.13. Found: C, 49.72; H, 4.61; N, 2.76; P, 6.25.

EXAMPLE 10

To a solution of ethyl N-trifluoroacetyl-N-(dichlorophosphonomethyl)glycinate (3.3 g, 0.01 mole) in 100 ml. of dry ether was added p-bromothiophenol (3.8 g, 0.02 mole) and triethylamine (2.02 g, 0.02 mole) in 50 ml. of dry ether. The solution was stirred for 16 hours at 20° C., filtered and the filtrate was concentrated in vacuo. The residual oil was extracted into hot petroleum ether and the extracts concentrated in vacuo. The residue was dissolved in ether and the ether solution was washed with water, dried over magnesium sulfate and concentrated to yield 4.6 g of ethyl N-trifluoroacetyl-N-(di(p-bromophenylthio)phosphonomethyl)glycinate as an opaque gum, $n_D^{22} = 1.6050$.

Anal. Calc'd: C, 35.92; H, 2.70; N, 2.20; P, 4.88. Found: C, 36.09; H, 2.77; N, 2.40; P, 4.79.

EXAMPLE 11

To a solution of ethyl N-trifluoroacetyl-N-(dichlorophosphonomethyl)glycinate (2.5 g, 0.0076 mole) in 100 ml. of dry ether was added sec-butyl mercaptan (1.37 g, 0.0152 mole) and triethylamine (1.54 g, 0.0152 mole) in 50 ml. of dry ether. The reaction was stirred for 16 hours at 20° C., then filtered. The filtrate was washed with water, dried over magnesium sulfate and concentrated in vacuo to yield ethyl N-trifluoroacetyl-N-(bis(-sec-butylthio)phosphonomethyl)glycinate (1.9 g), $n_D^{22} = 1.4839$.

Anal. Calc'd: C, 41.18; H, 6.22; N, 3.20; P, 7.08. Found: C, 41.02; H, 6.25; N, 3.34; P, 7.01.

EXAMPLE 12

To a solution of ethyl N-trifluoroacetyl-N-(dichlorophosphonomethyl)glycinate (2.5 g, 0.0076 mole) in 100 ml. of dry ether was added isobutylthiol (1.37 g, 0.0152 mole) and triethylamine (1.54 g, 0.0152 mole) in 50 ml. of dry ether. The reaction was stirred at 20° C. for 4 hours and then filtered. The filtrate was washed with water, dried over magnesium sulfate and concentrated in vacuo to afford ethyl N-trifluoroacetyl-N-(bis-(isobutylthio)phosphonomethyl)glycinate (2.2 g) as an oil, $n_D^{22} = 1.4821$.

EXAMPLE 13

To a solution of ethyl N-trifluoroacetyl-N-(dichlorophosphonomethyl)glycinate (3.3 g, 0.01 mole) in 100 ml. of dry ether was added p-fluorothiophenol (2.56 g, 0.02 mole) and triethylamine (2.02 g, 0.02 mole) in 60 ml. of ether. The reaction was stirred for 16 hours at 20° C., then filtered. The filtrate was washed with 3% aqueous ammonium hydroxide, dried over magnesium sulfate and concentrated in vacuo. The resulting oil was extracted into petroleum ether. The petroleum ether was concentrated in vacuo at 50° C. to afford ethyl N-trifluoroacetyl-N-(bis(p-fluorophenylthio)phosphonomethyl)glycinate (3.9 g) as an oil, $n_D^{22} = 1.5458$.

Anal. Calc'd: C, 44.45; H, 3.34; N, 2.73; P, 6.03. Found: C, 44.65; H, 3.26; N, 2.82; P, 5.94.

EXAMPLE 14

A solution of ethyl N-trifluoroacetyl-N-(dichlorophosphonomethyl)glycinate (4.95 g, 0.015 mole) in 150 ml. of dry ether was added to a solution of 4-bromo-3-methylthiophenol (6.1 g, 0.03 mole) and triethylamine (3.03 g, 0.03 mole) in 75 ml. of ether. The resulting solution was stirred at 20° C. for 16 hours, then filtered. The filtrate was concentrated in vacuo to afford 5.0 g of an oil which was chromatographed on silica gel eluting first with hexane to remove thiophenol, then with methylene chloride to afford 1.5 g of pure ethyl N-trifluoroacetyl-N-(bis(4-bromo-3-methylphenylthio)phosphonomethyl)glycinate as an oil, $n_D^{22} = 1.5918$.

EXAMPLE 15

To a solution of ethyl N-trifluoroacetyl-N-(dichlorophosphonomethyl)glycinate (3.3 g, 0.01 mole) in 150 ml. of dry ether was added triethylamine (1.92 g, 0.019 mole) in 20 ml. of ether followed by 2,5-dichlorothiophenol (3.4 g, 0.019 mole) in 30 ml. of ether. The resulting solution was stirred for four hours, then filtered. The filtrate was concentrated in vacuo and the residue extracted with 200 ml. hot petroleum ether. Concentration of the petroleum ether solution afforded a solid which was recrystallized from methylcyclohexane to yield ethyl N-trifluoroacetyl-N-(bis(2,5-dichlorophenylthio)phosphonomethyl)glycinate (2.6 g), m.p. 77°–80° C.

Anal. Calc'd: C, 37.09; H, 2.46; N, 2.28; P, 5.03. Found: C, 37.10; H, 2.56; N, 2.24; P, 5.11.

EXAMPLE 16

To a solution of ethyl N-trifluoroacetyl-N-(dichlorophosphonomethyl)glycinate (3.3 g, 0.01 mole) in 100 ml. of dry ether was added allyl mercaptan (2.1 g, 70%, 0.02 mole) and triethylamine (2.02 g, 0.02 mole) in 60 ml. of dry ether. The resulting solution was stirred at 20° C. for 48 hours. The mixture was filtered and the filtrate was concentrated in vacuo. The residue was chromatographed on silica gel eluting with methylene chloride to afford 4.1 g of pure ethyl N-trifluoroacetyl-N-(bis(allylthio)phosphonomethyl)glycinate as an oil, $n_D^{22} = 1.5101$.

Anal. Calc'd: C, 38.52; H, 4.72; N, 3.46; P, 7.64. Found: C, 38.66; H, 4.70; N, 3.84; P, 7.33.

EXAMPLE 17

To a solution of butyl N-trifluoroacetyl-N-(dichlorophosphonomethyl)glycinate (4.85 g, 0.0135 mole) in 200 ml. of dry ether was added m-thioanisole (3.8 g, 0.027 mole) and triethylamine (2.74 g, 0.027 mole) in 50 ml. of ether. The resulting mixture was stirred at 20° C. for four hours, then filtered. The filtrate was concentrated in vacuo to yield butyl N-trifluoroacetyl-N-(bis(m-methoxyphenylthio)phosphonomethyl)glycinate (7.25 g) as a viscous oil, $n_D^{22} = 1.5470$.

Anal. Calc'd: C, 48.84; H, 4.81; N, 2.84; P, 5.48. Found: C, 48.87; H, 4.90; N, 2.61; P, 5.29.

EXAMPLE 18

To a solution of n-butyl N-trifluoroacetyl-N-(dichlorophosphonomethyl)glycinate (7.2 g, 0.02 mole) in 100 ml. of ether was added a solution of methanethiol (1.92 g, 0.04 mole) and triethylamine (4.04 g, 0.04 mole) in 50 ml. of ether. After stirring for 16 hours at 20° C., the reaction mixture was filtered. The filtrate was concentrated in vacuo to yield an oil which was extracted with petroleum ether. The petroleum ether extracts were concentrated in vacuo to afford n-butyl N-trifluoroacetyl-N-(dithiomethylphosphonomethyl)glycinate (7.25 g) as an oil, $n_D^{22} = 1.4898$.

Anal. Calc'd: C, 34.64; H, 5.02; N, 3.67; P, 8.12. Found: C, 34.57; H, 5.11; N, 3.74; P, 8.33.

EXAMPLE 19

To a solution of β-chloroethyl N-trifluoroacetyl-N-(dichlorophosphonomethyl)glycinate (7.3 g, 0.02 mole) in 200 ml. of ether was added a solution of isopropylthiol (3.05 g, 0.04 mole) and triethylamine (4.04 g, 0.04 mole) in 100 ml. of ether. The resulting mixture was stirred at 20° C. for 96 hours, then filtered. The filtrate was concentrated in vacuo and the resulting oil was extracted with hot petroleum ether. Upon concentration, the extracts yielded β-chloroethyl N-trifluoroacetyl-N-(dithioisopropylphosphonomethyl)glycinate (7.25 g) as a golden oil, $n_D^{22} = 1.4959$.

Anal. Calc'd: C, 35.18; H, 5.00; N, 3.16; P, 6.98. Found: C, 35.31; H, 5.11; N, 3.06; P, 7.17.

EXAMPLE 20

To a solution of 2-methoxyethyl N-trifluoroacetyl-N-(dichlorophosphonomethyl)glycinate (6.3 g, 0.0175 mole) in 150 ml. of dry ether was added a solution of o-thiocresol (4.35 g, 0.035 mole) and triethylamine (3.5 g, 0.035 mole) in 50 ml. of dry ether. The resulting mixture was stirred for 96 hours at 20° C., then filtered. The filtrate was concentrated in vacuo and the residue was extracted into 500 ml. hot petroleum ether. Upon concentration, the extracts afforded an oil which slowly solidified. Recrystallization from heptane afforded 2-methoxyethyl N-trifluoroacetyl-N-(bis(o-thiocresyl)-phosphonomethyl)glycinate as a white solid, m.p. 64°–66.5° C.

Anal. Calc'd: C, 49.34; H, 4.71; N, 2.62; P, 5.78. Found: C, 49.46; H, 4.70; N, 2.72; P, 5.93.

EXAMPLE 21

To a solution of n-decyl N-trifluoroacetyl-N-(dichlorophosphonomethyl)glycinate (6.0 g, 0.0136 mole) in 150 ml. of dry ether was added a solution of methanethiol (1.3 g, 0.027 mole) and triethylamine (2.7 g, 0.027 mole) in 50 ml. of ether. The resulting mixture was stirred for 16 hours at 20° C., then filtered. The filtrate was concentrated in vacuo to afford n-decyl N-trifluoroacetyl-N-(dimethylthiophosphonomethyl)glycinate (6.0 g) as a light yellow oil, $n_D^{22} = 1.4811$.

Anal. Calc'd: C, 43.86; H, 6.71; N, 3.01; P, 6.65. Found: C, 43.81; H, 6.77; N, 3.08; P, 6.77.

EXAMPLE 22

To a solution of n-hexyl N-trifluoroacetyl-N-(dichlorophosphonomethyl)glycinate (7.7 g, 0.02 mole) in dry ether (200 ml.) was added a solution of methanethiol (1.9 g, 0.04 mole) and triethylamine (4.0 g, 0.04 mole) in 50 ml. of anhydrous ether. The resulting solution was stirred at 20° C. for three hours, then filtered. The filtrate was washed with water, then concentrated in vacuo to afford n-hexyl N-trifluoroacetyl-N-(bis(methylthio)phosphonomethyl)glycinate as a fluid yellow oil, $n_D^{25} = 1.4844$.

Anal. Calc'd: C, 38.14; H, 5.66; N, 3.42. Found: C, 37.89; H, 5.69; N, 3.42.

EXAMPLE 23

A solution of ethyl N-trifluoroacetyl-N-(dichlorophosphonomethyl)glycinate (3.95 g, 0.012 mole) in 150 ml. of ether at 0° C. was treated with a solution of p-chlorothiophenol (3.46 g, 0.024 mole) and triethylamine (2.4 g, 0.024 mole) in 50 ml. of ether. After stirring 16 hours at 25° C., the solution was filtered. The filtrate was washed with 10% aqueous sodium carbonate, dried over magnesium sulfate and concentrated in vacuo to yield ethyl N-trifluoroacetyl-N-(bis(p-chlorophenylthio)phosphonomethyl)glycinate (4.5 g) as a viscous oil, $n_D^{22} = 1.5695$.

Anal. Calc'd: C, 41.77; H, 3.14; N, 2.56. Found: C, 41.92; H, 3.33; N, 2.64.

EXAMPLE 24

To a solution of n-decyl N-trifluoroacetyl-N-(dichlorophosphonomethyl)glycinate (4.42 g, 0.01 mole) in 200 ml. of ether was added a solution of m-methylthiophenol (2.48 g, 0.02 mole) and triethylamine (2.02 g, 0.02 mole) in 50 ml. of ether. The resulting mixture was stirred for 16 hours at 20° C., then filtered. The filtrate was concentrated in vacuo to yield an oil which was chromatographed on silica gel (eluted with methylene chloride) to yield n-decyl N-trifluoroacetyl-N-(bis(m-methylphenylthio)phosphonomethyl)glycinate as an oil, $n_D^{27} = 1.5267$.

Anal. Calc'd: C, 55.58; H, 6.43; N, 2.23. Found: C, 55.15; H, 6.47; N, 2.37.

EXAMPLE 25

The post-emergence herbicidal activity of the various compounds of this invention is demonstrated by greenhouse testing in the following manner. A good grade of top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with soil and leveled. The pans are then placed on a sand bench in the greenhouse and watered from below as needed. After the plants reach the desired age (two to three weeks), each pan except for the control pans is removed individually to a spraying chamber and sprayed by means of an atomizer operating at a positive air pressure of approximately 1.46 kg/cm² absolute. The atomizer contains 6 ml. of a solution or suspension of the chemical and an amount of a cyclohexanone emulsifying agent mixture so that the spray solution or suspension contains about 0.4% by weight of the emulsifier. The spray solution or suspension contains a sufficient amount of the candidate chemical in order to give application rates corresponding to those set forth in the tables. The spray solution is prepared by taking an aliquot of a 1.0% by weight stock solution or suspension of the candidate chemical in an organic solvent such as acetone or tetrahydrofuran or in water. The emulsifying agent employed is a mixture comprising 35 weight percent butylamine dodecylbenzene sulfonate and 65 weight percent of a tall oil ethylene oxide condensate having about 11 moles of ethylene oxide per mole of tall oil. The pans are returned to the greenhouse and watered as before and the injury to the plants as compared to the control is observed at approximately two and four weeks as indicated in the tables under WAT and the results recorded. In some instances, the four-week observations are omitted.

The post-emergence herbicidal activity index used in Table I is as follows:

| Plant Response | Index |
|---|---|
| 0–24% control | 0 |
| 25–49% control | 1 |

| Plant Response | Index |
| --- | --- |
| 50-74% control | 2 |
| 75-99% control | 3 |
| 100% control | 4 |

The plant species utilized in these tests are identified by letter in accordance with the following legend:

A - Canada Thistle*  
B - Cocklebur  
C - Velvetleaf  
D - Morningglory  
E - Lambsquarters  
F - Smartweed  
G - Yellow Nutsedge*  
H - Quackgrass*  
I - Johnsongrass*  
J - Downy Brome  
K - Barnyardgrass  
L - Soybean  
M - Sugar Beet  
N - Wheat  
O - Rice  
P - Sorghum  
Q - Wild Buckwheat  
R - Hemp Sesbania  
S - Panicum Spp  
T - Crabgrass

*Established from vegetative propagules.

Table I

| Compound of Example Number | WAT | kg/h | A | B | C | D | E | F | G | H | I | J | K |
| --- | --- | --- | --- | --- | --- | --- | --- | --- | --- | --- | --- | --- | --- |
| 1 | 4 | 11.2 | 1 | 2 | 1 | 2 | 3 | 3 | 1 | 2 | 2 | 2 | 4 |
| 1 | 4 | 5.6 | 2 | 3 | 2 | 3 | 3 | 2 | 2 | 2 | 2 | 3 | 3 |
| 2 | 4 | 11.2 | 3 | 4 | 4 | 4 | 4 | 4 | 2 | 3 | 3 | 3 | 4 |
| 2 | 4 | 5.6 | 4 | 3 | 4 | 4 | 4 | 3 | 2 | 2 | 3 | 3 | 3 |
| 3 | 4 | 11.2 | 4 | 4 | 4 | 4 | 4 | 4 | 3 | 4 | 4 | 4 | 4 |
| 3 | 4 | 5.6 | 3 | 3 | 2 | 3 | 3 | 3 | 3 | 4 | 3 | 2 | 4 |
| 4 | 4 | 11.2 | 1 | 2 | 2 | 1 | 4 | 4 | 2 | 4 | 3 | 3 | 3 |
| 4 | 4 | 5.6 | 1 | 2 | 1 | 1 | 3 | 1 | 2 | 2 | 3 | 3 | 3 |
| 5 | 4 | 11.2 | 1 | 2 | 2 | 1 | 2 | 1 | 2 | 2 | 2 | 2 | 2 |
| 5 | 4 | 5.6 | 1 | 1 | 0 | 1 | 1 | 1 | 2 | 2 | 2 | 1 | 2 |
| 6 | 4 | 11.2 | 1 | 4 | 4 | 2 | 3 | 4 | 2 | 3 | 3 | 3 | 3 |
| 6 | 4 | 5.6 | 2 | 4 | 3 | 2 | 4 | 3 | 2 | 3 | 3 | 4 | 3 |
| 7 | 4 | 11.2 | 1 | 2 | 1 | 1 | 4 | 3 | 2 | 3 | 3 | 1 | 3 |
| 7 | 4 | 5.6 | 1 | 2 | 1 | 1 | 4 | 2 | 2 | 3 | 3 | 2 | 3 |
| 8 | 4 | 11.2 | 4 | 4 | 4 | 2 | 3 | 3 | 3 | 3 | 3 | 3 | |
| 8 | 4 | 5.6 | 2 | 2 | 2 | 1 | 2 | 2 | 2 | 3 | 2 | 3 | 3 |
| 9 | 4 | 11.2 | 4 | 2 | 3 | 2 | 4 | 3 | 3 | 3 | 3 | 4 | 4 |
| 9 | 4 | 5.6 | 1 | 2 | 2 | 1 | 3 | 2 | 2 | 2 | 2 | 3 | 3 |
| 10 | 4 | 11.2 | 1 | 2 | 3 | 2 | 4 | 3 | 2 | 3 | 2 | 2 | 3 |
| 10 | 4 | 5.6 | 1 | 1 | 1 | 1 | 2 | 2 | 2 | 2 | 2 | 2 | 3 |
| 11 | 4 | 11.2 | 2 | 3 | 3 | 2 | 3 | 3 | 4 | 3 | 3 | 3 | 4 |
| 11 | 4 | 5.6 | 1 | 2 | 3 | 1 | 3 | 1 | 2 | 1 | 2 | 2 | 3 |
| 12 | 4 | 11.2 | 1 | 2 | 2 | 1 | 2 | 2 | 2 | 3 | 2 | 3 | 3 |
| 12 | 4 | 5.6 | 1 | 1 | 2 | 1 | 2 | 2 | 1 | 2 | 2 | 2 | 3 |
| 13 | 4 | 11.2 | 1 | 2 | 2 | 4 | 4 | 4 | 2 | 2 | 2 | 1 | 3 |
| 13 | 4 | 5.6 | 1 | 2 | 2 | 1 | 4 | 4 | 1 | 1 | 1 | 1 | 4 |
| 14 | 4 | 11.2 | 1 | 2 | 2 | 2 | 4 | 4 | 2 | 1 | 2 | 1 | 3 |
| 14 | 4 | 5.6 | 1 | 1 | 1 | 1 | 3 | 3 | 1 | 1 | 2 | 1 | 3 |
| 15 | 4 | 11.2 | 1 | 3 | 1 | 1 | 4 | 4 | 2 | 1 | 1 | 1 | 3 |
| 15 | 4 | 5.6 | 2 | 2 | 1 | 1 | 4 | 3 | 1 | 1 | 1 | 2 | 2 |
| 16 | 4 | 11.2 | 2 | 4 | 4 | 4 | 4 | 4 | 3 | 3 | 2 | 3 | 3 |
| 16 | 4 | 5.6 | 2 | 3 | 4 | 4 | 4 | 4 | 3 | 2 | 2 | 3 | 3 |
| 17 | 4 | 11.2 | 1 | 1 | 0 | 1 | 1 | 1 | 1 | 0 | 1 | 1 | 2 |
| 18 | 4 | 11.2 | 2 | 2 | 2 | 2 | 3 | 1 | 2 | 2 | 3 | 4 | 3 |
| 18 | 4 | 5.6 | 4 | 1 | 1 | 2 | — | 1 | 1 | 1 | 3 | 3 | 2 |
| 19 | 4 | 11.2 | 3 | 3 | 2 | 2 | 4 | 1 | 2 | 1 | 3 | 2 | 3 |
| 19 | 4 | 5.6 | 2 | 2 | 2 | 2 | 2 | 1 | 2 | 2 | 3 | 2 | 3 |
| 20 | 4 | 11.2 | 1 | 2 | 1 | 1 | 0 | 0 | 1 | 1 | 0 | 1 | 1 |
| 21 | 4 | 11.2 | 1 | 2 | 1 | 1 | 0 | 0 | 1 | 0 | 2 | 1 | 2 |
| 22 | 4 | 11.2 | 2 | 2 | 2 | 1 | 3 | 4 | 2 | 3 | 3 | 4 | 3 |
| 22 | 4 | 5.6 | 0 | 2 | 1 | 2 | 3 | 4 | 1 | 4 | 3 | 3 | 3 |
| 23 | 4 | 11.2 | 2 | 3 | 3 | 2 | 3 | 3 | 1 | 2 | 2 | 3 | 4 |
| 23 | 4 | 5.6 | 1 | — | 2 | 3 | 3 | 3 | 1 | 2 | 3 | 1 | 4 |
| 24 | 4 | 56.0 | 1 | 2 | 0 | 2 | 2 | 1 | 1 | 1 | 1 | 1 | 1 |

Table II

| Compounds of Example No. | WAT | kg/h | L | M | N | O | P | B | Q | D | R | E | F | C | J | S | K | T |
| --- | --- | --- | --- | --- | --- | --- | --- | --- | --- | --- | --- | --- | --- | --- | --- | --- | --- | --- |
| 1 | 4 | 5.6 | 2 | 1 | 3 | — | 2 | 3 | 1 | 2 | 1 | 2 | 1 | 2 | 3 | 2 | 2 | 3 |
| 1 | 4 | 1.12 | 1 | 1 | 1 | 0 | 1 | 2 | 0 | 2 | 1 | 1 | 1 | 1 | 2 | 1 | 2 | 2 |
| 2 | 4 | 5.6 | 3 | 3 | 3 | 3 | 4 | 3 | 2 | 3 | 3 | 3 | 3 | 3 | 3 | 3 | 3 | 4 |
| 2 | 4 | 1.12 | 2 | 2 | 2 | 1 | 2 | 2 | 1 | 2 | 2 | 2 | 1 | 1 | 2 | 2 | 2 | 3 |
| 3 | 4 | 5.6 | 3 | 2 | 3 | 4 | 3 | 3 | 2 | 3 | 3 | 4 | 4 | 4 | 4 | 3 | 3 | 4 |
| 3 | 4 | 1.12 | 1 | 0 | 1 | 0 | 3 | 2 | 1 | 2 | 1 | 2 | 2 | 2 | 1 | 3 | 2 | 3 |
| 4 | 4 | 5.6 | 2 | 4 | 3 | 2 | 2 | 3 | 3 | 4 | 2 | 2 | 4 | 4 | 3 | 3 | 3 | 4 |
| 4 | 4 | 1.12 | 1 | 2 | 1 | 1 | 1 | 1 | 1 | 1 | 1 | 2 | 2 | 1 | 1 | 2 | 2 | 2 |
| 6 | 4 | 5.6 | 3 | 3 | 4 | 4 | 4 | 3 | 2 | 2 | 3 | 4 | 4 | 4 | 4 | 4 | 4 | 4 |
| 6 | 4 | 1.12 | 2 | 2 | 3 | 3 | 2 | 2 | 1 | 1 | 3 | 4 | 2 | 2 | 2 | 4 | 3 | 4 |
| 6 | 4 | 0.28 | 1 | 1 | 1 | 1 | 1 | 1 | 0 | 1 | 1 | 2 | 1 | 0 | 0 | 1 | 2 | 2 |
| 7 | 4 | 5.6 | 2 | 2 | 3 | 3 | 3 | 3 | 1 | 2 | 3 | 4 | 3 | 3 | 3 | 4 | 3 | 4 |
| 7 | 4 | 1.12 | 1 | 1 | 1 | 0 | 2 | 1 | 1 | 1 | 1 | 2 | 1 | 1 | 2 | 2 | 2 | 3 |
| 8 | 4 | 5.6 | 2 | 3 | 3 | 3 | 3 | 3 | 1 | 2 | 2 | 3 | 2 | 3 | 3 | 4 | 4 | 4 |

Table II-continued

| Compounds of Example No. | WAT | kg/h | L | M | N | O | P | B | Q | D | R | E | F | C | J | S | K | T |
|---|---|---|---|---|---|---|---|---|---|---|---|---|---|---|---|---|---|---|
| 8 | 4 | 1.12 | 1 | 1 | 2 | 1 | 2 | 2 | 1 | 1 | 1 | 3 | 2 | 2 | 2 | 3 | 2 | 3 |
| 9 | 4 | 5.6 | 2 | 4 | 3 | 3 | 3 | 3 | 1 | 2 | 2 | 4 | 3 | 2 | 3 | 4 | 4 | 4 |
| 9 | 4 | 1.12 | 1 | 1 | 2 | 1 | 2 | 1 | 0 | 1 | 2 | 3 | 2 | 1 | 1 | 2 | 2 | 2 |
| 10 | 4 | 5.6 | 2 | 2 | 3 | 4 | 3 | 3 | 2 | 2 | 4 | 4 | 4 | 3 | 4 | 4 | 3 | 4 |
| 10 | 4 | 1.12 | 1 | 1 | 1 | 0 | 1 | 1 | 0 | 1 | 1 | 2 | 1 | 1 | 1 | 3 | 2 | 3 |
| 11 | 4 | 5.6 | 1 | 3 | 3 | 4 | 3 | 3 | 4 | 2 | 4 | 4 | 4 | 3 | 4 | 4 | 3 | 4 |
| 11 | 4 | 1.12 | 1 | 1 | 1 | 0 | 1 | 1 | 1 | 1 | 1 | 2 | 2 | 1 | 2 | 3 | 2 | 3 |
| 11 | 4 | 0.28 | 1 | 1 | 0 | 0 | 1 | 1 | 1 | 1 | 1 | 1 | 0 | 1 | 2 | 2 | 1 | 2 |
| 12 | 4 | 5.6 | 2 | 4 | 3 | 2 | 2 | 2 | 1 | 1 | 4 | 3 | 4 | 3 | 4 | 4 | 3 | 4 |
| 12 | 4 | 1.12 | 1 | 1 | 1 | 0 | 1 | 1 | 0 | 1 | 1 | 2 | 2 | 1 | 2 | 2 | 2 | 3 |
| 13 | 4 | 5.6 | 3 | 3 | 3 | 3 | 4 | 3 | 2 | 3 | 4 | 4 | 4 | 3 | 4 | 4 | 4 | 4 |
| 13 | 4 | 1.12 | 1 | 3 | 3 | 1 | 2 | 2 | 2 | 2 | 4 | 4 | 3 | 1 | 2 | 3 | 3 | 4 |
| 13 | 4 | 0.28 | 1 | 1 | 1 | 0 | 0 | 1 | 0 | 1 | 2 | 3 | 1 | 1 | 0 | 1 | 2 | 2 |
| 14 | 4 | 5.6 | 2 | 4 | 4 | 2 | 3 | 3 | 2 | 3 | 4 | 4 | 4 | 4 | 4 | 4 | 3 | 4 |
| 14 | 4 | 1.12 | 1 | 3 | 2 | 1 | 2 | 2 | 1 | 2 | 3 | 4 | 2 | 1 | 1 | 4 | 3 | 3 |
| 14 | 4 | 0.28 | 0 | 1 | 0 | 0 | 0 | 0 | 0 | 1 | 1 | 1 | 0 | 0 | 0 | 1 | 1 | 1 |
| 15 | 4 | 5.6 | 2 | 4 | 4 | 1 | 3 | 2 | 2 | 3 | 4 | 4 | 4 | 3 | 3 | 4 | 3 | 4 |
| 15 | 4 | 1.12 | 0 | 1 | 2 | 1 | 1 | 2 | 1 | 2 | 2 | 2 | 2 | 1 | 0 | 4 | 2 | 4 |
| 16 | 4 | 5.6 | 4 | 4 | 4 | 4 | 4 | 4 | 4 | 4 | 4 | 4 | 4 | 4 | 4 | 4 | 4 | 4 |
| 16 | 4 | 1.12 | 1 | 1 | 2 | 1 | 1 | 2 | 1 | 2 | 1 | 3 | 1 | 2 | 2 | 3 | 3 | 3 |
| 16 | 4 | 0.28 | 1 | 1 | 1 | 0 | 0 | 1 | 0 | 2 | 1 | 1 | 0 | 0 | 0 | 2 | 2 | 2 |
| 18 | 4 | 5.6 | 2 | 4 | 4 | 3 | 3 | 3 | 3 | 3 | 2 | 4 | 4 | 3 | 4 | 4 | 4 | 4 |
| 18 | 4 | 1.12 | 1 | 0 | 3 | 2 | 3 | 2 | 1 | 2 | 0 | 4 | 3 | 1 | 3 | 4 | 3 | 3 |
| 19 | 4 | 5.6 | 2 | 1 | 4 | 3 | 4 | 3 | 2 | 2 | 1 | 4 | 3 | 2 | 3 | 3 | 3 | 4 |
| 19 | 4 | 1.12 | 1 | 1 | 1 | 0 | 1 | 2 | 1 | 3 | 0 | 1 | 1 | 1 | 1 | 2 | 2 | 3 |
| 22 | 4 | 5.6 | 1 | 2 | 4 | 3 | 3 | 2 | 2 | 2 | 2 | 4 | 4 | 3 | 3 | 4 | 3 | 4 |
| 23 | 4 | 1.12 | 1 | 1 | 1 | — | 2 | 1 | 0 | 2 | 1 | 0 | 0 | 0 | 1 | 2 | 2 | 3 |
| 23 | 4 | 5.6 | 2 | 3 | 3 | — | 3 | 2 | 2 | 3 | 2 | 4 | 2 | 3 | 3 | 3 | 3 | 4 |

EXAMPLE 26

The pre-emergent herbicidal activity of various compounds of this invention is demonstrated as follows. A good grade of top soil is placed in aluminum pans and compacted to a depth of 0.95 to 1.27 cm. from the top of each pan. A predetermined number of seeds or vegetative propagules of each of several plant species are placed on top of the soil in each pan and then pressed down. Herbicidal compositions prepared as in the previous example are applied by admixture with or incorporation in the top layer of soil.

In this method, the soil required to cover the seeds and propagules is weighed and admixed with a herbicidal composition containing a known amount of the active ingredient (compound of this invention). The pans are then filled with the admixture and leveled. Watering is carried out by permitting the soil in the pans to absorb moisture through apertures in the pan bottoms. The seed and propagule containing pans are placed on a wet sand bench and maintained for approximately two weeks under ordinary conditions of sunlight and watering. At the end of this period, the number of emerged plants of each species is noted and compared to an untreated control. The data is given in the following table.

The pre-emergent herbicidal activity index used below is based upon average percent control of each species as follows:

| Percent Control | Index |
|---|---|
| 0-24% control | 0 |
| 25-49% control | 1 |
| 50-74% control | 2 |
| 75-100% control | 3 |

Plant species in the table are identified by the same code letters used in the previous example.

Table III

| Compound of Example No. | WAT | kg/h | A | B | C | D | E | F | G | H | I | J | K |
|---|---|---|---|---|---|---|---|---|---|---|---|---|---|
| 2 | 2 | 11.2 | 3 | 0 | 0 | 0 | 0 | 0 | 0 | 2 | 1 | 1 | 0 |
| 3 | 4 | 11.2 | 3 | 0 | 0 | 1 | 2 | 0 | 1 | 2 | 1 | 0 | 0 |
| 4 | 2 | 11.2 | 3 | 0 | 0 | 0 | 0 | 1 | 0 | 2 | 0 | 1 | 1 |
| 5 | 2 | 11.2 | 3 | 0 | 0 | 0 | 0 | 0 | 0 | 0 | 0 | 0 | 0 |
| 6 | 2 | 11.2 | 3 | 0 | 0 | 0 | 1 | 0 | 1 | 3 | 0 | 0 | 0 |
| 7 | 2 | 11.2 | 3 | 0 | 0 | 0 | 1 | 0 | 3 | 3 | 2 | 0 | 0 |
| 8 | 2 | 11.2 | 3 | 0 | 0 | 0 | 3 | 0 | 2 | 2 | 0 | 0 | 0 |
| 9 | 2 | 11.2 | 3 | 0 | 0 | 0 | 0 | 0 | 1 | 1 | 1 | 0 | 0 |
| 10 | 2 | 11.2 | 3 | 0 | 0 | 0 | 0 | 1 | 1 | 1 | 0 | 0 | 0 |
| 11 | 4 | 11.2 | 2 | 0 | 1 | 0 | 0 | 0 | 0 | 0 | 0 | 2 | 0 |
| 12 | 4 | 11.2 | 3 | 0 | 0 | 0 | 3 | 0 | 0 | 2 | 0 | 1 | 0 |
| 13 | 2 | 11.2 | 3 | 0 | 0 | 0 | 0 | 0 | 0 | 2 | 0 | 0 | 0 |
| 14 | 2 | 11.2 | 2 | 0 | 0 | 0 | 0 | 0 | 0 | 0 | 0 | 0 | 0 |
| 15 | 2 | 11.2 | 1 | 0 | 0 | 0 | 0 | 0 | 1 | 0 | 0 | 0 | 0 |
| 16 | 2 | 11.2 | 3 | 0 | 0 | 0 | 0 | 0 | 1 | 0 | 0 | 1 | 0 |
| 17 | 2 | 11.2 | 1 | 0 | 0 | 0 | 0 | 0 | 0 | 0 | 0 | 0 | 0 |
| 18 | 4 | 11.2 | 3 | 1 | 0 | 2 | 3 | 1 | 3 | 3 | 1 | 3 | 2 |
| 19 | 4 | 11.2 | 3 | 0 | 1 | 0 | 3 | 0 | 2 | 0 | 0 | 1 | 0 |
| 22 | 2 | 11.2 | 3 | 0 | 0 | — | 3 | 0 | 0 | 0 | 1 | 0 | 1 |

From the test results presented in Tables I and II, it can be seen that the post-emergent herbicidal activity of the compounds of this invention is, for the most part, general in nature. In certain specific instances, however, some selectivity is demonstrated. In this regard it should be recognized that each individual species selected for the above tests is a representative member of a recognized family of plant species.

From Table III, it can be seen that the pre-emergent herbicidal activity demonstrated some selectivity.

The herbicidal compositions, including concentrates which require dilution prior to application to the plants, of this invention contain from 5 to 95 parts by weight of at least one compound of this invention and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, acetone, tetrahydrofuran, all parts being by weight of the total composition. Preferably, the compositions of this invention contain from 5 to 75 parts by weight of at least one compound of this invention, together with the adjuvants. Where required, from about 0.1 to 2.0 parts by weight of the inert liquid extender can be replaced by a corrosion inhibitor or anti-foaming agent, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent", it is understood that wetting agents, dispersing agents, suspending agents and emulsifying agents are included therein. Anionic, cationic and nonionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin, sulfonates, polymeric alkyl naphthalene sulfonates, sodium naphthalene sulfonate polymethylene bisnaphthalenesulfonate and sodium N-methyl-N-(long chain acid) taurates.

When operating in accordance with the present invention, effective amounts of the compounds or compositions of this invention are applied to the plants, or to soil containing the plants, or are incorporated into aquatic media in any convenient fashion. The application of liquid and particulate solid compositions to plants or soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds or compositions of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycine employed. In foliar treatment for the control of vegetative growth, the active ingredients are applied in amounts from about 0.112 to about 22.4 or more kilograms per hectare. In pre-emergent treatments, the rate of application can be from about 0.56 to about 22.4 or more kilograms per hectare. In applications for the control of aquatic plants, the active ingredients are applied in amounts of from about 0.01 parts per million to about 1000 parts per million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound of the formula

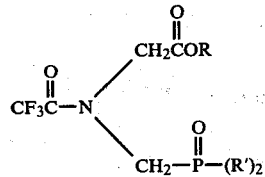

wherein R is an alkyl group containing from 1 to 10 carbon atoms, a chloro lower alkyl group containing from 1 to 4 carbon atoms and 1 to 3 chlorine groups, a lower alkoxy lower alkyl group containing from 3 to 6 carbon atoms or an alkoxyalkoxyalkyl group containing from 5 to 9 carbon atoms and R' is a member of the group consisting of lower alkylthio, lower alkenylthio, benzylthio, phenylthio, or substituted phenylthio wherein the phenyl group contains 1 to 2 substituents selected from the group consisting of halo, lower alkyl and lower alkoxy.

2. A compound of claim 1 wherein R' is a lower alkylthio, lower alkenylthio or benzylthio group.

3. A compound of claim 1 wherein R' is a phenylthio or a substituted phenylthio group.

4. A compound as defined in claim 2 which is ethyl N-trifluoroacetyl-N-(dithiomethylphosphonomethyl)-glycinate.

5. A compound as defined in claim 2 which is ethyl N-trifluoroacetyl-N-(di-n-propylthiophosphonomethyl)glycinate.

6. A compound as defined in claim 2 which is ethyl N-trifluoroacetyl-N-(bis(allylthio)phosphonomethyl)glycinate.

7. A compound as defined in claim 3 which is ethyl-N-trifluoroacetyl-N-(diphenylthio)phosphonomethylglycinate.

8. A compound as defined in claim 3 which is ethyl N-trifluoroacetyl-N-(bis(2,5-dichlorophenylthio)phosphonomethylglycinate.

9. A herbicidal composition comprising an inert adjuvant and a herbicidally effective amount of a compound of the formula

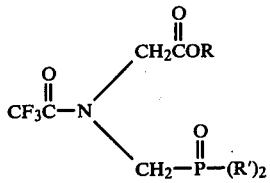

wherein R is an alkyl group containing from 1 to 10 carbon atoms, a chloro lower alkyl group containing from 1 to 4 carbon atoms and 1 to 3 chlorine groups, a lower alkoxy lower alkyl group containing from 3 to 6 carbon atoms or an alkoxyalkoxyalkyl group containing from 5 to 9 carbon atoms and R' is a member of the group consisting of lower alkylthio, lower alkenylthio, benzylthio, phenylthio, or substituted phenylthio wherein the phenyl group contains 1 to 2 substituents selected from the group consisting of halo, lower alkyl and lower alkoxy.

10. A herbicidal composition of claim 9 wherein R' is a lower alkylthio, lower alkenylthio or benzylthio group.

11. A herbicidal composition of claim 9 wherein R' is a phenylthio or a substituted phenylthio group.

12. A herbicidal composition of claim 10 wherein the compound is ethyl N-trifluoroacetyl-N-(dithiomethylphosphonomethyl)glycinate.

13. A herbicidal composition of claim 10 wherein the compound is ethyl N-trifluoroacetyl-N-(di-n-propylthiophosphonomethyl)glycinate.

14. A herbicidal composition of claim 10 wherein the compound is ethyl N-trifluoroacetyl-N-(bis(allylthio)phosphonomethyl)glycinate.

15. A herbicidal composition of claim 11 wherein the compound is ethyl N-trifluoroacetyl-N-(diphenylthio)phosphonomethylglycinate.

16. A herbicidal composition of claim 11 wherein the compound is ethyl N-trifluoroacetyl-N-(bis(2,5-dichlorophenylthio)phosphonomethylglycinate.

17. A herbicidal method which comprises contacting a plant or the plant growth medium with a herbicidally effective amount of a compound of the formula

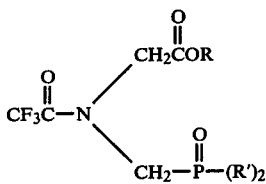

wherein R is an alkyl group containing from 1 to 10 carbon atoms, a chloro lower alkyl group containing from 1 to 4 carbon atoms and 1 to 3 chlorine groups, a lower alkoxy lower alkyl group containing from 3 to 6 carbon atoms or an alkoxyalkoxyalkyl group containing from 5 to 9 carbon atoms and R' is a member of the group consisting of lower alkylthio, lower alkenylthio, benzylthio, phenylthio, or substituted phenylthio wherein the phenyl group contains 1 to 2 substituents selected from the group consisting of halo, lower alkyl and lower alkoxy.

18. A herbicidal method of claim 17 wherein R' is a lower alkylthio, lower alkenylthio or benzylthio group.

19. A herbicidal method of claim 17 wherein R' is a phenylthio or a substituted phenylthio group.

20. A herbicidal method of claim 18 wherein the compound is ethyl N-trifluoroacetyl-N-(dithiomethylphosphonomethyl)glycinate.

21. A herbicidal method of claim 18 wherein the compound is ethyl N-trifluoroacetyl-N-(di-n-propylthiophosphonomethyl)glycinate.

22. A herbicidal method of claim 18 wherein the compound is ethyl N-trifluoroacetyl-N-(bis(allylthio)phosphonomethyl)glycinate.

23. A herbicidal method of claim 19 wherein the compound is ethyl N-trifluoroacetyl-N-(diphenylthio)phosphonomethylglycinate.

24. A herbicidal method of claim 19 wherein the compound is ethyl N-trifluoroacetyl-N-(bis(2,5-dichlorophenylthio)phosphonomethylglycinate.

* * * * *